US009791439B2

(12) United States Patent
Vivien et al.

(10) Patent No.: US 9,791,439 B2
(45) Date of Patent: *Oct. 17, 2017

(54) MULTI-TARGET PHOTONIC BIOSENSOR, AND METHOD FOR MANUFACTURING AND PREPARING SAME

(75) Inventors: Laurent Vivien, Vauhallan (FR); Etienne Gaufres, Vergeze (FR); Nicolas Izard, Palaiseau (FR); Eric Doris, Orsay (FR); Edmond Gravel, L'Hay les Roses (FR); Didier Boquet, Les Pavillions sous Bois (FR)

(73) Assignees: UNIVERSITE PARIS SUD 11, Orsay (FR); CENTRE NATIONAL DE LA RECHERCHE SCIENTIFIQUE, Paris (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 314 days.

This patent is subject to a terminal disclaimer.

(21) Appl. No.: 13/983,093

(22) PCT Filed: Feb. 9, 2012

(86) PCT No.: PCT/FR2012/050287
§ 371 (c)(1),
(2), (4) Date: Aug. 1, 2013

(87) PCT Pub. No.: WO2012/168589
PCT Pub. Date: Dec. 13, 2012

(65) Prior Publication Data
US 2013/0316368 A1    Nov. 28, 2013

(30) Foreign Application Priority Data
Feb. 9, 2011 (FR) .................................. 11 51042

(51) Int. Cl.
*G01N 33/543* (2006.01)
*G01N 21/45* (2006.01)
(Continued)

(52) U.S. Cl.
CPC ....... *G01N 33/54386* (2013.01); *C08G 61/02* (2013.01); *G01N 21/45* (2013.01);
(Continued)

(58) Field of Classification Search
None
See application file for complete search history.

(56) References Cited

U.S. PATENT DOCUMENTS

2009/0140167 A1 * 6/2009 Ward et al. ................ 250/458.1
2010/0259752 A1   10/2010 Shah et al.
2011/0246086 A1   10/2011 Huang et al.

FOREIGN PATENT DOCUMENTS

EP        1918693        5/2008
WO    WO2008046010    *  4/2008
(Continued)

OTHER PUBLICATIONS

E. Adam et al., "Electroluminescene from Single-Wall Carbon Nanotube Network Transistors", Nano Letters, vol. 8, No. 8, 2008.
(Continued)

*Primary Examiner* — Rebecca Martinez
(74) *Attorney, Agent, or Firm* — Greer, Burns & Crain, Ltd.

(57) ABSTRACT

A component or device is provided for the detection or the measurement in parallel of one or more specific types of biological or chemical target products. This component includes a group of nanotubes selected and/or functionalized to interact with the target product, around an optical waveguide. Thus, an optical coupling is produced between the optical waveguide and one or more optical characteristics of
(Continued)

these nanotubes, the modifications of which are evaluated in the presence of the target product. In addition, a method is provided for manufacturing and preparing such a component or device, and a detection method using them, as well as a post-manufacture preparation method comprising a specific functionalization for different target products starting from the same type of pluripotent generic component. Also provided is a family of PFO-based functionalization polymers.

11 Claims, 7 Drawing Sheets

(51) Int. Cl.
  *G01N 21/64* (2006.01)
  *G01N 21/77* (2006.01)
  *C08G 61/02* (2006.01)
  *B82Y 15/00* (2011.01)
  *B82Y 40/00* (2011.01)

(52) U.S. Cl.
  CPC ....... *G01N 21/648* (2013.01); *G01N 21/7703* (2013.01); *G01N 21/7746* (2013.01); *B82Y 15/00* (2013.01); *B82Y 40/00* (2013.01); *G01N 2021/7776* (2013.01); *G01N 2021/7779* (2013.01); *G01N 2021/7783* (2013.01); *G01N 2021/7789* (2013.01)

(56) References Cited

FOREIGN PATENT DOCUMENTS

WO   2008/069454   6/2008
WO   2009/095710   8/2009

OTHER PUBLICATIONS

Mathias Steiner et al., "Carbon Nanotubes and Optical Confinement: Controlling Light Emission in Nanophotonic Devices", Proceedings of SPIE, Sep. 9, 2008.
Xia Fengnian et al., "A Microcavity-Controlled, Current-Driven, On-Chip Nanotube Emitter at Infrared Wavelengths", Nature Nanotechnology, vol. 3, No. 10, Oct. 2008.
Patigul Imin et al., "Supramolecular Complexes of Single Walled Carbo Nanotubes with Conjugated Polymers", Polymer Chemistry, vol. 2, 2011, pp. 411-416.
Fuyong Cheng et al., "Soluble, Discrete Supramolecular Complexes of Single-Walled Carbon Nanotubes with Fluorene-Based Conjugated Polymers", Macromolecules, vol. 41, 2008, pp. 2304-2308.
Elena Bekyarova et al., "Mechanism of Ammonia Detection by Chemically Functionalized Single-Walled Carbon Nanotubes: In Situ Electrical and Optical Study of Gas Analyte Detection", J. Am. Chem. Soc., vol. 128, 2007, pp. 10700-10706.
M. Consales et al., "Simultaneous Detection of Organic Vapors by Optical Fiber and Acoustic Sensors Based on Single-Walled Carbon Nanotubes", Proceedings of SPIE, vol. 5855, May 23, 2005, pp. 46-49.

* cited by examiner

MULTI-TARGET PHOTONIC BIOSENSOR, AND METHOD FOR MANUFACTURING AND PREPARING SAME

BACKGROUND

The present invention relates to a component or device for detecting or measuring one or more specific types of biological or chemical target products. According to the invention, such a component comprises a group of one or more nanotubes selected and/or functionalized in order to interact with the target product, and which surrounds or runs alongside an optical waveguide over all or part of its periphery. This component thus produces an optical coupling between a portion of this optical waveguide and one or more optical characteristics of these nanotubes, the modifications of which are evaluated in the presence of the target product.

The invention also relates to a method for manufacturing and preparing such a component or device, and a detection method using it.

It also relates to a post-manufacture preparation method comprising a specific functionalization depending on a plurality of different target products, starting from the same type of pluripotent generic component, which is not yet functionalized.

TECHNICAL FIELD

The qualitative and/or quantitative detection of specific biological or chemical substances is very useful in numerous research and industrial fields, for example medical or chemical, and in particular for preventing or treating health problems by making an early and accurate diagnosis.

In the biological field, this detection can be for example a detection of cancer cells or toxins, or a measurement of biological parameters such as glucose or insulin levels for the screening and monitoring of diabetes, or any other biological substance or substance present in an organism or a biological medium. Such a detection makes it possible to make a therapeutic diagnosis, which allows rapid treatment of patients thanks to screening for the disease in the first stages of its development. It is therefore useful to have effective detection systems making it possible to reveal minute traces of biological agents in an extremely small volume. It is also important to have inexpensive means that are easy to use, in order to allow numerous, easily-accessible analyses.

In the chemical field, it may be a matter of detecting particular substances which can affect an environment being monitored, for example pollutants in the air or in the water, or catalysts or contaminants within a reactive medium in the context of a chemical process in the general sense of the term.

Biosensors can be defined as a combination of a biological receptor (a molecule having a particular affinity for a single type of molecules or cells to be detected) with a physical or physico-chemical transducer which supplies a signal representing the presence or the quantity of these specific molecules or cells to be detected within a medium to be tested.

In the present document, the term "biosensor" must be understood to mean suited to molecules or cells in the biological field, but also to other types of chemical molecules or groups to be detected which would be farther from the field usually referred to as "biological".

Among the different types of biosensors that exist, a significant proportion uses an introduction of markers inside the medium to be tested, for example radioactive isotopes or fluorescent molecules.

Types of biosensors without markers are less numerous and often more recent, but have a certain number of advantages. As they do not use any markers, they do not require a preliminary step of incorporation of the markers into the medium to be tested. This avoids damaging this medium, limits interferences in the detection, and avoids the risks of contamination in particular in the case of detection in vivo. Furthermore, they often allow more rapid evaluation of the detection and thus make it possible to measure the molecular interaction in real time, for example in order to study the kinetics of this interaction or of a biological mechanism in progress.

The currently known optical technologies of biosensors without markers are based on optical circuits the waveguide of which is functionalized by implanting on its surface receptor molecules specific to a product to be detected. When they bind to the product to be detected, these receptors modify the optical characteristics of the waveguide, which is detected by evaluation of an optical signal passing along the waveguide.

For example, in the document WO200869454, this waveguide is a diffraction grating produced by parallel grooves bearing a fine highly refractive optical layer of a precise thickness, deposited before etching using a wet type deposition process. Antibodies sensitive to the antigens to be detected are bound to this optical layer in the upper parts of the grooves, and modify the behaviour of an optical signal passing through this grating within a guided mode resonance filter.

In the document WO200995710, with a similar functionalization, it is sought to improve the sensitivity and selectivity by partially covering with metal a spiral resonant optical guide within a photonic crystal with a lattice of holes, in order to also use a plasmon effect on the surface of the metal layer.

In the document US 2010/259752, the waveguide is an optical fibre made of silica ($SiO_2$) comprising a Bragg grating, on which carbon nanotubes are directly grown, aligned and perpendicular to the surface of the fibre. The growth of these nanotubes on the fibre requires a sequence of complex operations which must sometimes be repeated several times, and which can be carried out only in the laboratory or factory. This formation of nanotubes usually comprises at least:
  plasma etching, then
  an application of catalyst, which can require a complex process such as electrolytic or plasma deposition, then heating to 500° C. or even 1000° C., and
  formation of the nanotubes by a CVD (Chemical Vapour Deposition) process.

These nanotubes can be functionalized by carboxyl, amine, nitrate and hydroxyl chemical groups.

When they react to a biochemical element or to a physical parameter such as a radiation or a sonic wave, these nanotubes modify the specific functional spectrum of the Bragg grating with which they are "infused".

The known technologies, however, have limits, for example in terms of sensitivity and also because they do not always allow simple and inexpensive mass production and are often limited to the detection of a single type of target. When they make it possible to carry out several types of detection, the choice of the product to be detected is established and fixed when the circuits are manufactured, and each of the different circuits must be available when different products are to be detected.

Moreover, a device allowing multi-detection in parallel becomes extremely complex to produce, since it is then necessary to functionalize each sensor, one after the other with different receptors, within demanding steps of production all of which involve very difficult manufacturing procedures, for example requiring the use of clean room equipment and/or an etching reactor and/or a specific reactor for depositing the receptors.

SUMMARY

A purpose of the invention is to remedy the drawbacks and limits of the prior art, in particular with respect to the following points:
  providing sensitive and specific detection;
  simple use and reliable operation;
  under simple and economic manufacturing conditions;
  with good flexibility during implementation and at the design stage as needed;
  limiting the risks of interference and contamination;
  allowing a rapid reading or reading in real time, and/or in parallel;
  for a plurality of different targets in parallel, or even simultaneously;
  small space requirement.

For this, the invention proposes a component for detecting or measuring at least one specific type of so-called "target" biological or chemical products, for example an organic cell, a macromolecule, or even a simple body or a simple chemical compound, in liquid or gaseous form. This detection component is of the type providing a light signal or electronic signal representing the presence, or even a quantity, of target product in a biological or chemical medium to be tested when this medium to be tested is brought into contact with part of this sensor comprising at least one optical waveguide element the operation of which is modified by the presence of the target product in question.

According to the invention, this component also comprises a group of one or more nanotubes at least some of which are semiconducting nanotubes, which are selected and/or functionalized in order to interact with this target product. This group of nanotubes surrounds the optical waveguide over all or part of its periphery, for example in contact therewith or at least inside an optical mode existing in this waveguide. This group of nanotubes induces an optical coupling, in a so-called coupling portion of this guide, between
  on the one hand an optical signal transmitted or received in this coupling portion of the optical waveguide, and
  on the other hand one or more optical characteristics of these nanotubes, for example photoluminescence, or fluorescence, or refractive index, or absorption, which are modified by the presence of the target product.

Typically, the nanotubes in the group are predominantly, for example more than 80%, or even exclusively semiconducting nanotubes.

A good solution is to use semiconducting carbon nanotubes, for example but not necessarily of single-walled type (SWCNT).

In a currently preferred embodiment, the nanotubes in the group are functionalized in order to interact with the target product thanks to receptors which are bound to these nanotubes. These receptors are chosen specifically in order to interact or bind specifically to the target product to be detected. They can be for example antibodies corresponding to an antigen present on biological cells to be detected, such as for example cancer cells or white blood cells infected with HIV. They can also be of any known type, present or future, of molecules or macromolecules binding specifically and/or easily to a specific chemical biological product that is to be detected, liquid or gaseous.

These receptors can be bound to the nanotubes in different ways, for example by known methods such as grafting methods using chemical spacers.

According to a feature, the invention also proposes to carry out the selection and/or the functionalization of the nanotubes using a polymer.

According to this feature, the receptors are bound to the nanotubes via chains of at least one so-called functionalization polymer, in particular a polymer derived from PFO, which is chosen or produced in order to be able to receive at least one type of receptor. The long chains of such a polymer are bound to the surface of these nanotubes, for example by surrounding them several times under the effect of their physico-chemical properties.

Preferably, the functionalization polymer chosen is of a type capable of receiving a plurality of types of receptors, specific to different target products.

PFO within the strict meaning of the term is a homopolymer of fluorene groups, and is for example produced by Aldrich company. Its chains have a tendency to wrap around certain nanotubes, for example depending on their nature and/or their chirality. Its use is known for selecting certain types of nanotubes, for example semiconducting, for example by mixing in the form of gel followed by centrifugation.

According to an aspect of the invention, an original polymer is proposed, comprising or constituted by a copolymer predominantly based on fluorene-type monomers, including functionalization monomers distributed for example in the form of a random copolymer.

The general structure of such a functionalization polymer can be represented in the following form:

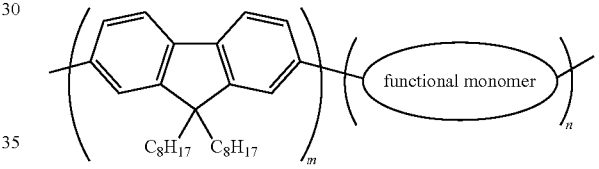

with a proportion of functionalization monomers comprised between 1% and 20% of the chain total, for example 10% i.e. an m/n ratio substantially equal to 9.

Preferably, the functionalization monomer is based on a fluorene group to which one or two functionalization groups "$Fn_1$" and "$Fn_2$" are attached.

Each of these groups "$Fn_1$" and "$Fn_2$" can be chosen for example from the following group:
  $SH$; $NH_2$; $N_3$; $OCH_2CO_2R'$; $C_8H_{17}$;

The functionalization polymer, or PFO-f, can then be represented as follows:

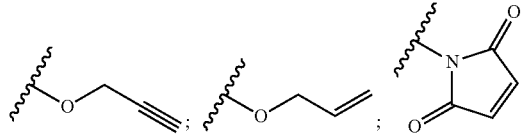

with: $1 \leq x \leq 6$ and $1 \leq m/n \leq 9$ (typically x=6 and m/n=9).

By way of example, the functionalization monomer can be obtained in one of the following ways and in one of the following forms:

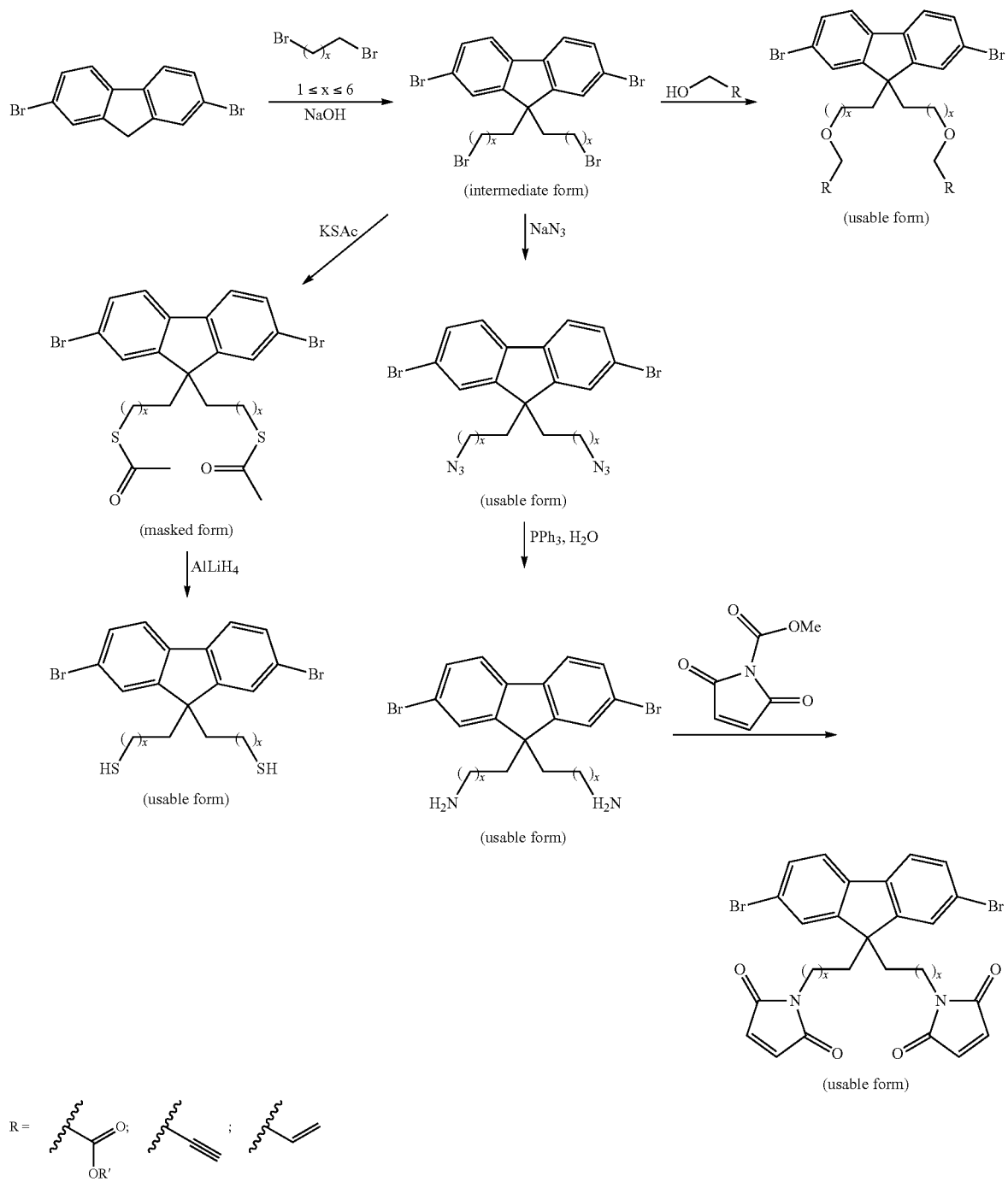
The functionalization polymer can then be obtained, for example, as follows:
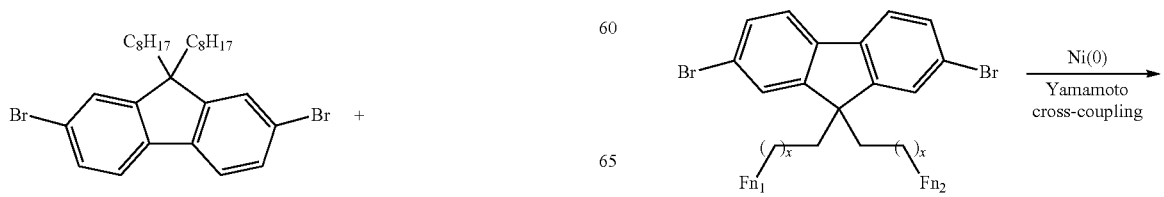

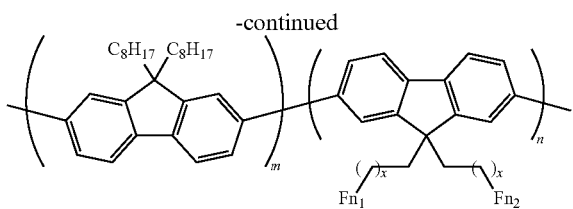

with: 1≤x≤6 and 1≤m/n≤9 (typically x=6 and m/n=9); and:

$Fn_1$=SH; $NH_2$; $N_3$; $OCH_2CO_2R'$; $C_8H_{17}$; $Fn_2$=SH; $NH_2$; $N_3$; $OCH_2CO_2R'$; $C_8H_{17}$;

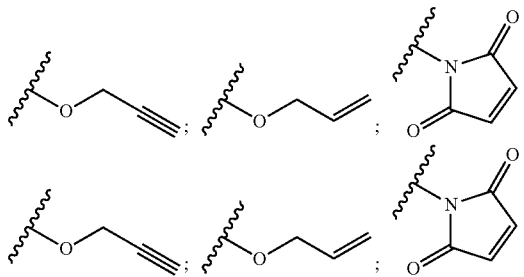

It should be noted that such a functionalization polymer can be used in order to functionalize nanotubes in all the different embodiments described here, but also in other applications using a variation of the physico-chemical properties (including optical) of the nanotubes in the presence of one or more target products.

According to another aspect, the invention also proposes a device for detecting one or more specific types of target biological and/or chemical products, comprising a plurality of sensors each including at least one component as disclosed here. These sensors are arranged so as to interact simultaneously and independently of each other with the same medium to be tested, for example by being integrated in the same substrate, adjacent to one another or joined together within the same surface area of less than 5 cm², or even 1 cm².

These different sensors can be for example connected, multiplexed or in parallel, to an electronic device arranged in order to interpret and/or transmit their information and to control their operation and activation.

This device can in particular comprise at least two differently functionalized sensors for detecting or measuring two different target products.

It can be seen that it is thus possible to obtain multiple simultaneous measurements from the same medium to be tested, for example for several different target products, or with different sensor calibrations or sensitivities making it possible to obtain a wider range of measurable quantities.

In a preferred embodiment, the invention proposes in particular to use a waveguide comprising a coupling portion arranged in order to obtain a evanescent mode which confines the electromagnetic wave around all or some of the nanotubes in the group.

It also proposes to provide a coupling portion enclosed in or connected to an optical element of a known type carrying out an optical amplification or an optical detection of the optical modifications of the nanotubes which originate from their interaction with the target product. This optical detection or amplification element can for example be a ring resonator, a Mach-Zehnder interferometer or a Fabry-Perot cavity, with photonic crystals or standard waveguides.

The invention can be carried out in particular with a silicon-based optical waveguide, i.e. crystalline semiconducting silicon, or even silicon nitride and within a silicon photonic circuit, for example of SOI ("Silicon On Insulator") type, the technology of which is economical, well controlled and very widespread.

Studies of nanotubes have shown that these materials can have certain semiconductor-type properties due to their nanometric scale, and their one-dimensional nature.

Thus, the publication "Electroluminescence from Single-Wall Carbon Nanotube Network Transistors" by Adam et al. in NanoLetters 2008, 8 (8) 2351-2355, presents a multidirectional electroluminescent effect obtained in a field-effect transistor produced by applying an electric field between several successive parallel electrodes arranged across a track constituted either by a single nanotube (CNFET), or by a unorganized network of several nanotubes (NNFET).

In the publications "Carbon Nanotubes and Optical Confinement—Controlling Light Emission in Nanophotonic Devices" by Steiner et al. in SPIE 2008 vol. 703713 703713, and "A microcavity-controlled, current-driven, on-chip nanotube emitter at infrared wavelengths" by Fengnian et al. in Nature Nanotechnology Vol. 3 Oct. 2008, it was proposed to pick up such an electroluminescent effect using an optical "amplification" microcavity.

According to the invention, by using nanotubes graded for their optical properties with a surface coating selected or modified in order to induce a selective interaction with the chosen targets, the sensitivity of the nanotubes to their environment makes it possible to obtain a modulation of their optical properties in contact with such targets.

As the nanotubes are extremely sensitive to their environment, the binding of a molecule or biomolecule to their surface induces transfers of charges, disturbing their photonic and electronic properties. The interaction between the guided mode in the photonic structure and the nanotube network brings about an increase in the sensitivity and the specificity of the entire detection system.

Initial studies show that the silicon photonic structures coupled with carbon nanotube networks allow the detection of low concentrations of biological substances with a sensitivity of less than 1 pg/mm2.

Such photonic biosensors make it possible to obtain an inexpensive solution, for example by producing single-use sensors which moreover provide good safety which are compact and have a small space requirement with a surface area of the order of mm² (for example between 0.5 and 5 mm²); easy to use and allowing multiple analyses in parallel, for example allowing the simultaneous detection of several types of infectious or symptomatic molecules, by several sensors integrated on the same substrate and differently functionalized.

It can be seen that the invention thus makes it possible to obtain a particularly sensitive and specific photonic biosensor with small dimensions, which is flexible and has a variety of uses, and which can be produced in large quantities and with economic costs.

In the same way, the invention also proposes a method for manufacturing or preparing a component or device for the detection of at least one specific type of target product, of biological or chemical nature in liquid or gaseous form, of the type supplying a light signal or electronic signal representing the presence or even a quantity of this target product in a biological or chemical medium to be tested, when this medium to be tested is brought into contact with part of this component comprising at least one optical waveguide element the operation of which is modified by the presence of this same target product.

According to the invention, this manufacturing method comprises:
on the one hand at least one operation of selection and/or functionalization of at least one group of one or more nanotubes by a procedure chosen in order to cause this group to interact with this target product, and
on the other hand at least one operation of putting into place such a group of nanotubes so as to surround this optical waveguide over all or part of its periphery, and thus induce an optical coupling in a so-called coupling portion of this guide, between an optical signal transmitted or received in this coupling portion of the optical waveguide, and one or more optical characteristics of these nanotubes, which optical characteristics are modified by the presence of the target product in question.

Preferably, the operation of selection and/or functionalization of at least one group of nanotubes comprises the following steps:
selection of non-metallic semiconducting nanotubes, preferably of a specific chirality, for example depending on the desired gap and for example in order to obtain a gap of 1.5 μm;
functionalization of the surface of said nanotubes by binding to their surface so-called receptor molecules which are chosen in order to interact or bind specifically to said target product.

In a preferred embodiment of the invention, the operation of selection and/or functionalization of at least one group of nanotubes comprises the following steps:
selection of the nanotubes by binding or interaction of a plurality of nanotubes with at least one polymer, in particular a derivative of PFO, chosen to be capable on the one hand of receiving one or preferably several types of receptors, and on the other hand of binding specifically to at least one specific type of nanotubes, for example determined by their semiconducting nature and/or with respect to their chirality, thus carrying out a first so-called initial functionalization;
second, so-called specific, functionalization, of said nanotubes by binding of so-called specific receptor molecules, chosen to be capable of interacting with or binding to the target product, on the polymer chains bound to these nanotubes.

It should be noted that the operations of depositing the nanotubes and binding the receptors have far fewer technological restrictions than the production of the optical circuits, or even than the assembly and the mounting of the electronic environment around these optical circuits.

Thus, the invention makes it possible to carry out certain parts of the manufacture and preparation of the sensors in a much simpler, more economical and less restrictive environment, for example without the need for a clean room, nor for specific and difficult elements such as etching and/or deposition reactors.

It is thus possible to produce, in the factory, sensors that are not functionalized, or that have been subjected only to "initial" functionalization. These more or less "blank", or generic, sensors can then be finally functionalized in a less restrictive environment and possibly at short notice.

This final functionalization can then be carried out by "grafting" a pre-functionalized or "initialized" generic sensor, already provided with nanotubes but without receptors, by using different types of receptors depending on the detection needs. It can also be carried out by integrating, on a blank generic sensor without nanotubes, a small quantity of already functionalized nanotubes, chosen depending on the detection needs within a stock of several varieties of completely functionalized nanotubes (with their specific receptors).

BRIEF DESCRIPTION OF THE DRAWINGS

Various embodiments of the invention are provided, which according to the set of their possible combinations, incorporate the different optional characteristics disclosed here.

Other characteristics and advantages of the invention will become apparent from the detailed description of an embodiment which is in no way limitative, and the attached drawings in which:

FIG. 5: with a Fabry-Pérot cavity,
FIG. 6: with a Mach-Zehnder interferometer,
and
FIG. 7: with a ring resonator;

DETAILED DESCRIPTION

Production and Preparation: First Embodiment

Figure 1:
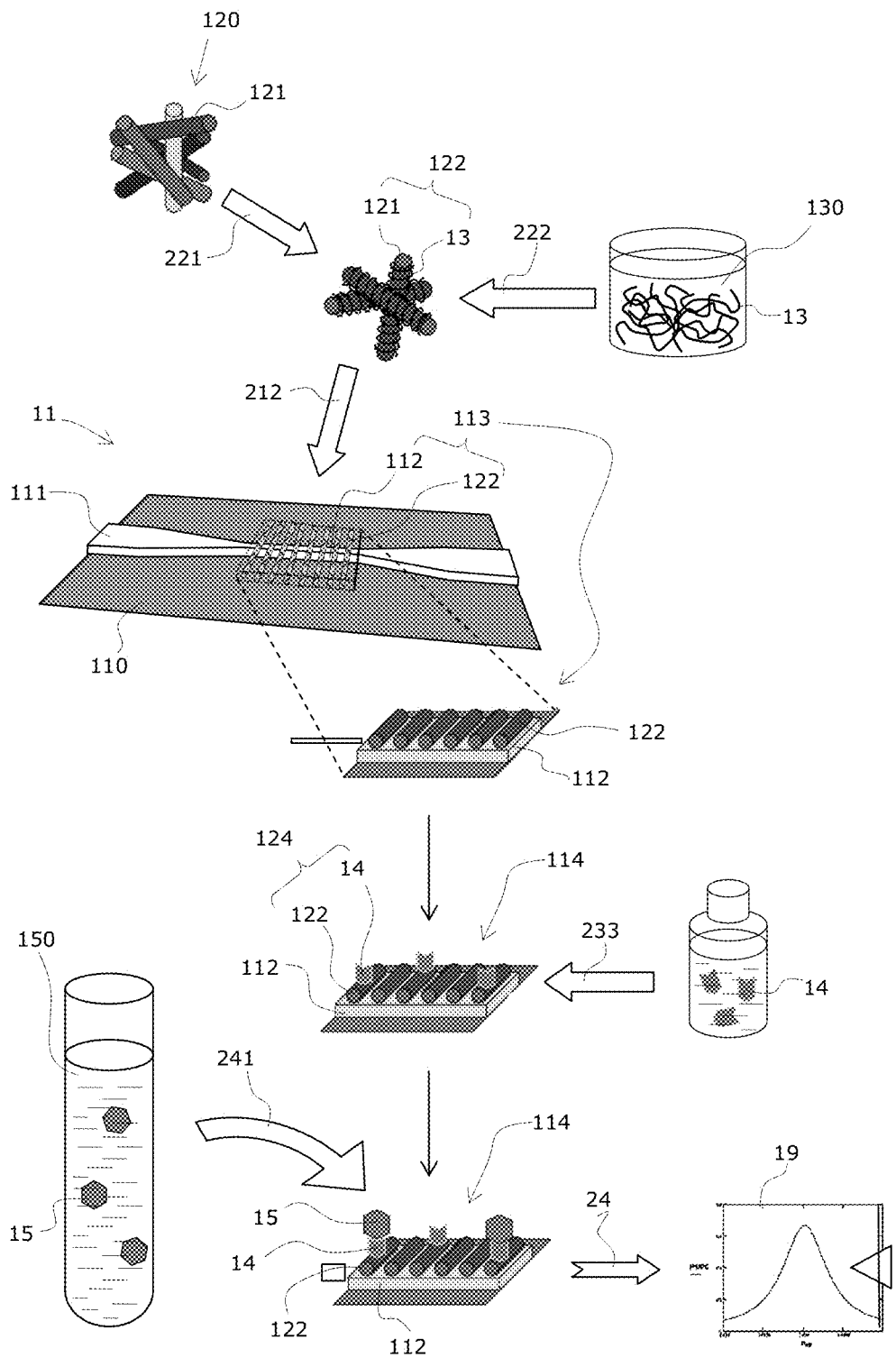
FIG. 1 and FIG. 2 are respectively a schematic diagram and a flowchart illustrating the manufacture, preparation and use of a sensor according to the invention in a first embodiment, with specific functionalization after application of the nanotubes.
Figure 2:
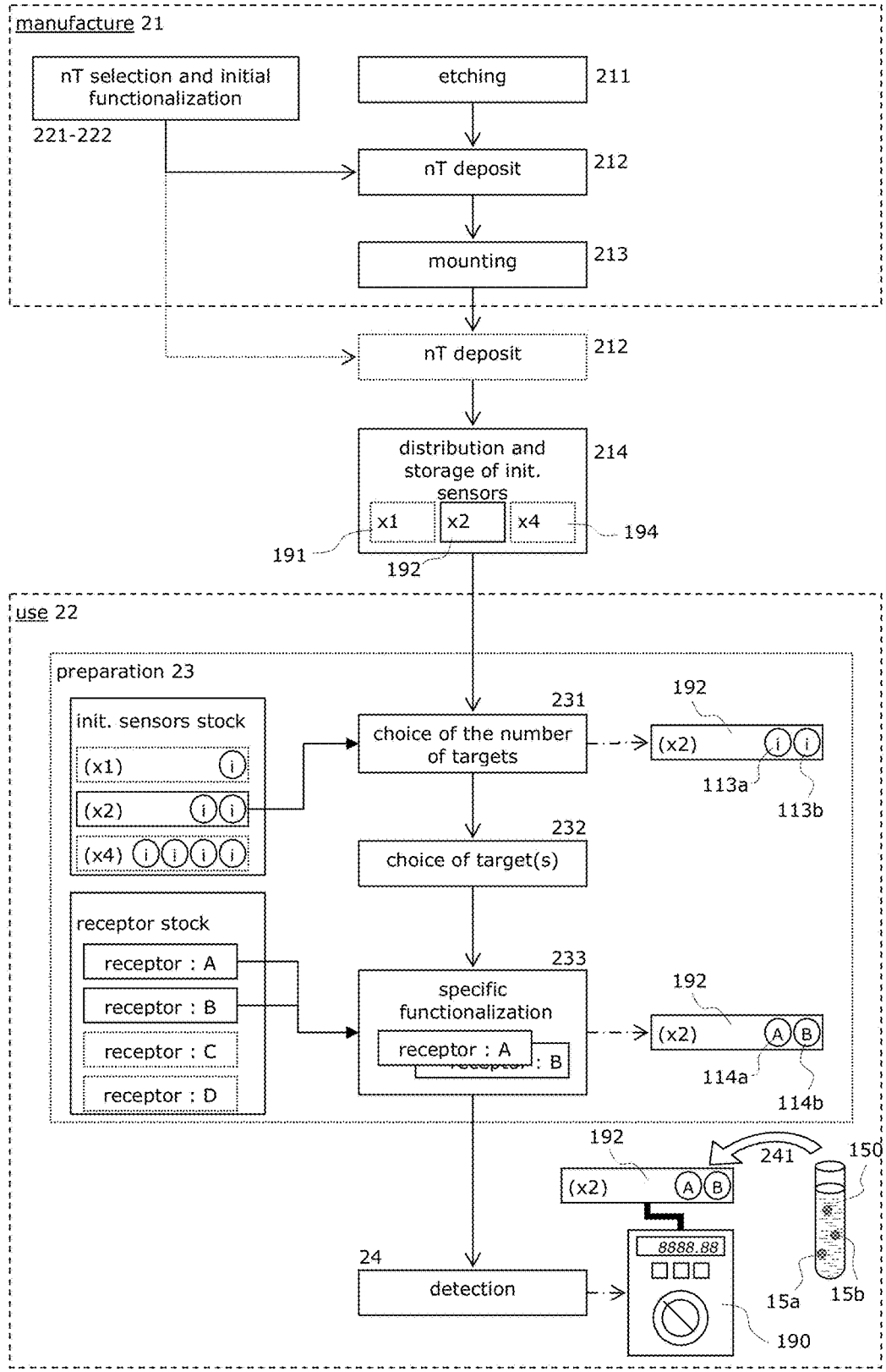

FIG. 1 and FIG. 2 show different steps of the manufacture, preparation and use of a sensor according to the invention in a first embodiment.

A manufacturing procedure 21 is carried out in a standard manufacturing environment for photonic and electronic components, and by means known in these fields.

In this manufacturing procedure 21, the manufacture of the optical circuit is carried out, including typically an etching phase 211, for example on an SOI base or "wafer", for example by known technologies for producing integrated photonic or optronic circuits. In this phase, an optical waveguide 111 is produced on a base or a substrate 110.

By way of example, the operations 211, 411 for producing one or more optical circuits can be carried out by the following techniques:

The materials used are silicon (Si) or silicon nitride ($Si_3N_4$) for the material with a high refractive index, i.e. the core of the guide, and silica ($SiO_2$) for the material with a low index, i.e. the coating; as well as silicon (Si) for the substrate.

The patterns can be exposed to light by electron-beam lithography, and preferably deep ultraviolet and nano-imprint lithography.

The silicon or the silicon nitride can be etched using the RIE (Reactive Ion Etching) or ICP (Inductively Coupled Plasma) process.

Metal electrodes can optionally be deposited with a view to subsequently aligning the nanotubes by dielectrophoresis, then removed if necessary by RIE or chemical attack.

During this manufacturing procedure 21 or independently in parallel, nanotubes are prepared equipped with a first surface functionalization, here referred to as "initial" functionalization and producing "initialized" nanotubes 122. For this, semiconducting nanotubes 121 are used, for example possibly single-walled carbon nanotubes (SWNT) preferably chosen with the same specific chirality.

These selected nanotubes 121 then receive a surface functionalization using polymer chains 13 comprising anchoring sites making it possible to subsequently bind the desired specific receptor or receptors 14.

By way of non-exclusive example, the selection 121 and the initial functionalization 122 can be carried out together by causing a medium 120 of nanotubes of varying kinds to interact with a medium containing a functionalization polymer 13 chosen for its affinity for the carbon nanotubes, for example a polyfluorene derivative which will be called hereinafter: "PFO-f". By causing these to interact with each other, for example by mixing the nanotubes 120 with a gel 130 containing this polymer 13, functionalized 122 semiconducting nanotubes 121 are obtained. These functionalized nanotubes are then separated from the others 120, for example by using their different density via a method such as a centrifugation.

A greater or lesser quantity, which can even be limited to a single nanotube 122, is then deposited 212 on the optical guide 111 in a specific portion which thus becomes, or contains, the coupling portion 112. This "group" of initialized nanotubes 122 can optionally be more strongly bound using complementary procedures, for example by deposition of metal on the nanotubes 122 outside the coupling zone 112.

This association of the nanotubes 122 and the coupling portion 112 thus forms a detection zone 113, which can be replicated at several different sites on the same optical circuit 11, for example in order to combine detection of several target products in a single measurement.

A single detection device or detector 191, 192 or 194 can moreover comprise several detection zones 113a and 113b respectively, produced within several different optical circuits, independent in their amplification and measurement part, thus forming a plurality of independent unitary sensors on the same multi-measurement detector.

Such detection devices, which can be called single-measurement detectors 191 or multi-measurement detectors 192 and 194, can be produced in a compact and simple form, for example strictly limited to the optical circuit alone or completed solely by the optronic components ensuring the evaluation of the detection light signals. Such minimal detectors, for example completely integrated in a simple substrate plate or on a chip or an electronic card, can then be connected to an electronic or optronic device 190 for controlling and operating the detection light signals.

At the end of the manufacturing procedure 21, it is thus possible to obtain, distribute and store 214 one or more types of detectors, single-measurement 191 with a single detection zone 113 or multi-measurement 192, 194 for example with two detection zones 113a, 113b and four detection zones respectively. These detectors can be manufactured in large quantities and for a very economical unit cost and for example suitable and intended for single use in combination with a reusable operating device 190.

It should be noted that the preparation and the deposition of the nanotubes 122 do not require installations as complex and expensive as the production 211 of the optical circuit itself, or even as the assembly and mounting 213 of the optical circuit within mechanical and/or electronic elements 190 arranged in order to produce a detector 191, 192, 194.

As shown in dotted lines in FIG. 2, the deposition 212 of the nanotubes on the coupling portion 112 can thus be carried out at different times in the manufacturing procedure 21, before or after this mounting 213, or even outside the procedure 21 and the manufacturing installations.

Furthermore, it will be noted that the sensors and detectors thus manufactured and distributed are only initialized, but can still serve for several types of target products. The number of models to be manufactured and managed is thus limited, and does not depend, or depends only slightly, on the different types of target products 15 for which they will be used 24.

A final preparation procedure 23 is carried out in order to adapt the sensor or sensors 113a and 113b of each detector 191, 192 or 194 before carrying out the detection 24 itself.

Although this preparation can be carried out during the manufacturing procedure 21, the characteristics of the invention make it possible to delay this preparation phase 23 until the procedure of use 22. This preparation 23 can be done for example directly on site or possibly in a simpler workshop or laboratory, without a clean room or an etching reactor, by the user's personnel or by a relatively unspecialized technician employed by the user, distributor or installer.

Depending on the detection need or a particular command from the user, a choice 231 is made of a detector 192 provided with the necessary number of sensors, for example two sensors 113a and 113b in the example of FIG. 2. In this embodiment, the sensors 113a and 113b are already "initialized", as indicated in FIG. 2 by the "i" inside the circle of each sensor, as they already each comprise their group of nanotubes 122 provided with the polymer 13 and its anchoring sites, i.e. with their initial functionalization.

Depending on a choice 232 of the target product or products 15a and 15b to be detected, the receptor or receptors 14a and 14b suitable for carrying out a specific functionalization 233 of each of the sensors 113a and 113b of the chosen detector 192 are used.

These receptors 14, 14a, 14b, 14c, 14d are of very different kinds according to the choice of the target products to be detected, and are known or will be developed independently of the present invention. Their definition and their production are not included within the scope of the present invention, which will moreover be capable of implementation in a similar manner with future receptors not yet developed to date, provided that they have similar characteristics of affinity for the polymer or polymers 13 used for the initial functionalization 221 of the nanotubes 121.

As illustrated in FIG. 1, for each of the sensors to be functionalized, the chosen receptor 14 is made to interact with the initialized nanotubes 122. The receptor molecules 14 then bind to the anchoring sites of the polymer 13 which surrounds the surface of the nanotubes. Thus a so-called "finalized" 114 or "specifically functionalized" detection zone is obtained, i.e. specifically depending on the choice of the target product 15. In FIG. 2, the circle representing "finalized" sensors 114a and 114b is marked with the letter "A" or "B" corresponding respectively to the target product 14a or 15b for which these sensors have been specifically functionalized.

When this finalized detection zone 114 is put into the presence 241 of a medium 150 containing the target product, the molecules 15 of the target product will interact with or even bind to the receptor molecules 14 present on the nanotubes 122. The presence of the target product 15 will then modify the photonic characteristics of the nanotubes 122 of the detection zone 114, which will be detected 19 via an evaluation of a specific optical signal injected into the optical circuit 11.

In the case of a detector 192 with several adjacent sensors on a small surface area, for example two sensors 113a and 113b initialized but not yet specifically functionalized, it will be possible to separately finalize each of the initialized zones with different receptors 15a and respectively 14b. Thus two finalized sensors 114a and 114b respectively will be obtained for two different target products 14a and 15b respectively. The same medium 150 can then be tested with the two sensors 114a and 114b of the same detector 192, for example by pouring a drop onto the part of the detector 192 grouping these two sensors or by injecting the solution to be analyzed using a fluid system, or by introducing this region of the detector into an enclosure or inside a living human or animal body. Thus two independent measurements will be obtained in parallel, controlled and operated independently of each other by one or more pieces of apparatus 190, in parallel and/or multiplexing, thus providing simultaneous detection in real time of the different target products 15a and 15b in the same medium 150.

Because the different receptors 14a to 14d can be produced and stored independently of the detectors 191 to 194, it can be seen that the invention allows great flexibility in manufacture, storage, distribution and use. It is thus possible to reduce costs and storage volumes and precautions for the detectors and pieces of apparatus, and to make a multiple detection and screening easy to implement on site and easier and more affordable to implement on a large scale.

This first embodiment allows a particularly easy specialization of the sensors, by limiting the user's preparation operations to grafting the receptors. The operations of deposition and possibly of binding the nanotubes to the sensors, which can involve additional restrictions or work, have already been carried out in advance.

Production and Preparation: Second Embodiment

Figure 3:
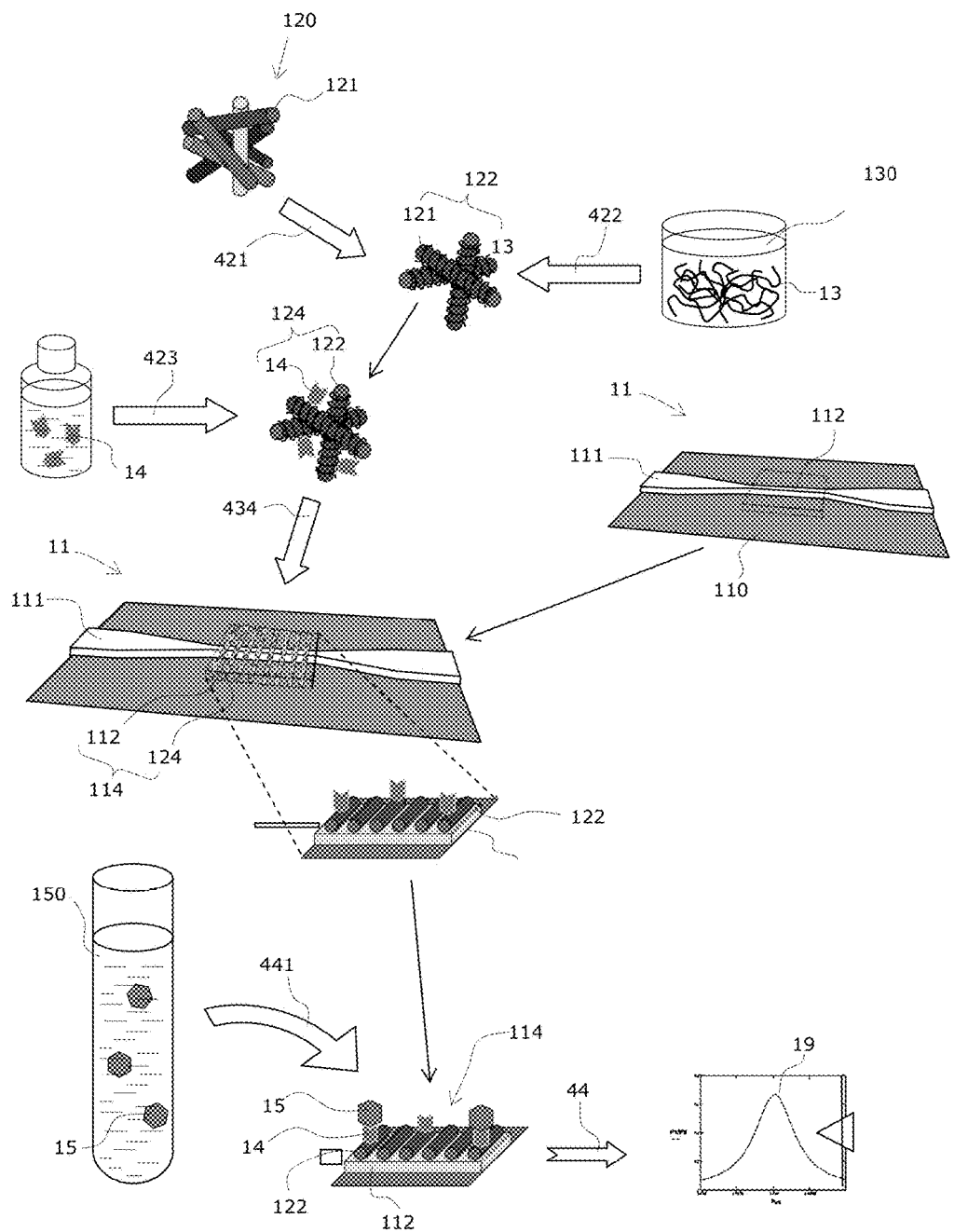
FIG. 3 and FIG. 4 are respectively a schematic diagram and a flowchart illustrating the manufacture, preparation and use of a sensor according to the invention in a second embodiment, with specific functionalization before application of the nanotubes.
Figure 4:
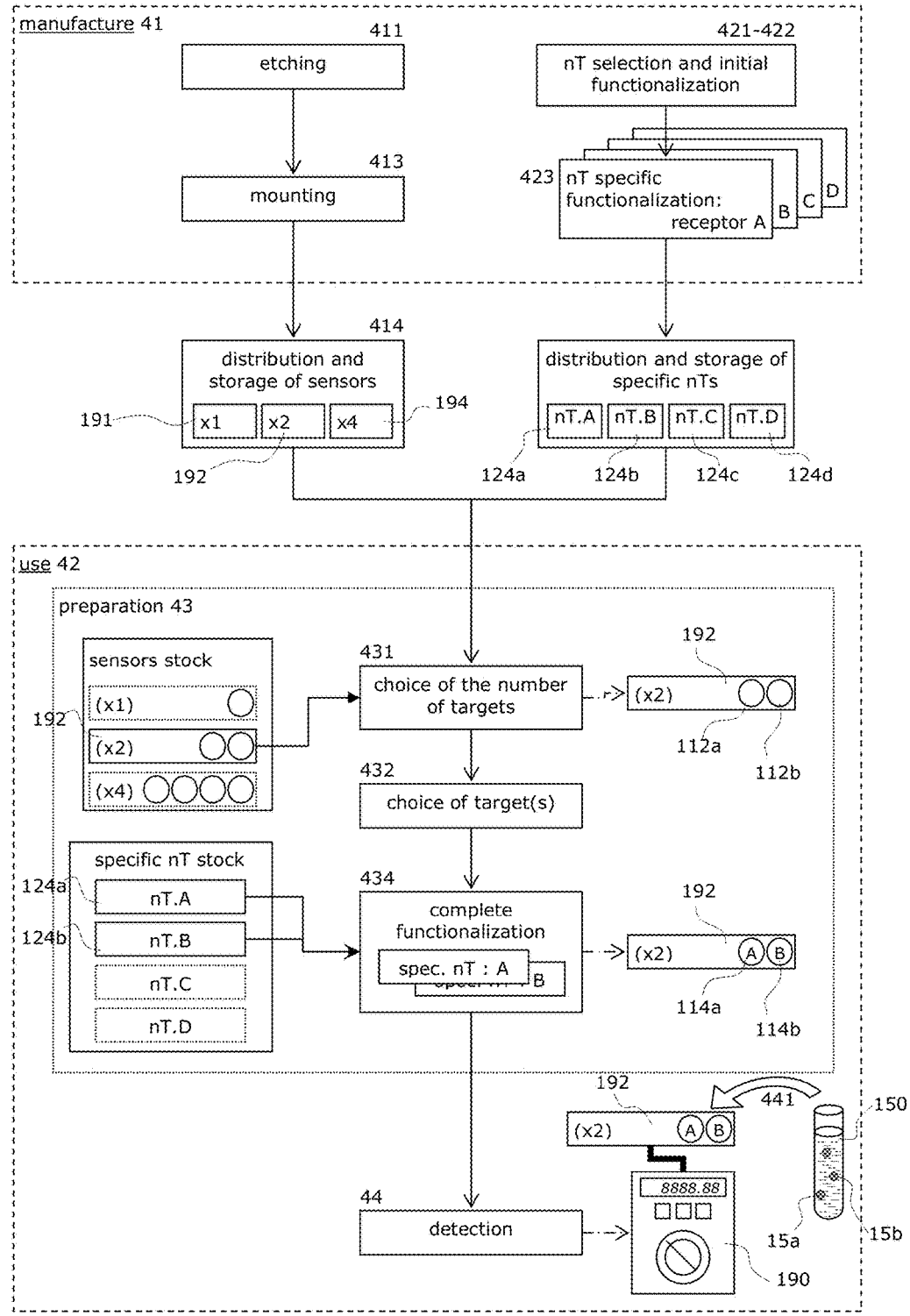

FIG. 3 and FIG. 4 show different steps of the manufacture, preparation and use of a sensor according to the invention in a second embodiment, which will be described in detail only where it differs from the first embodiment.

During the manufacturing procedure 41, the optical circuit is produced 411 and assembled 412 in order to produce detectors 191, 192, 194 each provided with one or more so-called "blank" sensors 112, 112a, 112b, i.e. the detection zone 112 of which has not yet received any nanotubes. These detectors are distributed and stored 414 in this blank form.

In parallel, nanotubes 121 are selected 421 and receive 422 an initial functionalization. They are then specifically functionalized 423 by interaction with a receptor 14, chosen from a type 14a-14d or from another, depending on different target products A-D.

Different types nT.A, nT.B, nT.C and nT.D of "specific" nanotubes thus completely functionalized are stored and distributed independently of each other.

It should be noted that the preparation 421, 422 and 423 of the specific nanotubes 124 does not require installations as complex and expensive as the production 411 of the optical circuit itself, or even as the assembly and the mounting 413 of the optical circuit within mechanical and/or electronic elements arranged to produce a detector 191, 192, 194.

A final preparation procedure 43 is carried out in order to adapt the sensor or sensors 112a and 112b of each detector 191, 192 or 194 before carrying out the detection 44 itself.

Although this preparation can be carried out during the manufacturing procedure 41, the characteristics of the invention make it possible to delay this preparation phase 43 until the procedure of use 42. This preparation 43 can be carried out for example directly on site or possibly in a simpler workshop or laboratory, without a clean room or an etching reactor, by the user's personnel or by a relatively unspecialized technician employed by the user, distributor or installer.

Depending on the detection need or a particular command from the user, a choice is made 431 of a detector 192 provided with the necessary number of sensors, for example two sensors 113a and 113b in the example of FIG. 4. In this embodiment, the sensors 113a and 113b are also "blank", as indicated in the figure by the empty circle for each sensor, as they do not yet comprise their nanotubes.

Depending on a choice 432 of the target product or products 15a and 15b to be detected, the specific type or types of nanotubes 124a and 124b suitable for carrying out a specific functionalization 433 of each of the sensors 112a and 112b of the chosen detector 192 are used. For this, a small quantity of the chosen specific nanotubes is deposited on and bound to each sensor 112a and 112b. Thus a detector 192 with several sensors 114a and 114b finalized for different target products 15a and 15b is obtained.

In the same manner as described previously, this detector 192 with two sensors 114a and 114b can then be used to detect 44, 441 two products 15a and 15b simultaneously and in real time in the same medium to be tested 15.

In a manner similar to the first embodiment, the production and the storage of the detectors are here dissociated from their specialization with respect to target products. Because the different types of finalized nanotubes 124a to 124d can be produced and stored independently of the detectors 191 to 194, it can be seen that the invention allows great flexibility in manufacture, storage, distribution and use. It is thus possible to reduce the costs and the storage volumes and precautions for the detectors and pieces of apparatus, and to make multiple detection and screening easier to implement on site and easier and more affordable to implement on a large scale.

This second embodiment can for example make it possible to have blank sensors which can receive nanotubes initialized with different polymers, for example in order to use a range of types of receptors in which the receptors are not all compatible with the same polymer but require different polymers.

Configurations of Sensors

FIG. 5 to FIG. 12f show different configurations of sensors according to the invention, which can be obtained according to different embodiments of the manufacture and preparation procedure, including the first and second embodiments described above.

FIG. 5 to FIG. 9 show schematic diagrams of example photonic circuits which can be used to produce a sensor according to the invention, in particular based on carbon nanotubes. In these circuits, different types of circuits are used to convert to optical intensity variation the effects of target-receptor coupling in the vicinity of the carbon nanotubes.

Figure 5:
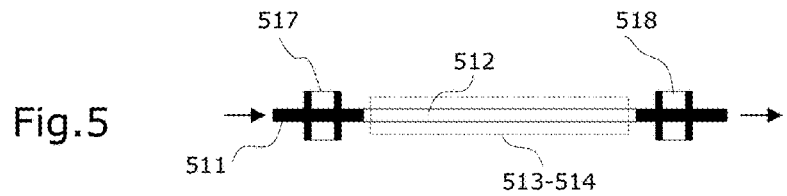
FIG. 5, FIG. 6 and FIG. 7 are respectively schematic diagrams illustrating example photonic circuits of sensors according to the invention, according to the following configurations.

In FIG. 5, the circuit comprises a straight optical guide 511, including a coupling portion 512 between two mirrors 517 and 518, produced for example by Bragg gratings, forming a Fabry-Perot cavity. The detection zone 513 (initialized) or 514 (finalized) is formed by a group of functionalized or finalized nanotubes deposited on the coupling portion 512 of the guide 511. A signal is for example injected on the left side and resonates in the Fabry-Perot cavity depending on the photonic characteristics, for example the absorption, resulting from the optical coupling between the guide portion 512 and the nanotubes. The characteristics of the output signal are modified by the presence or absence of molecules of the target product corresponding to the receptor grafted onto the nanotubes.

Figure 6:
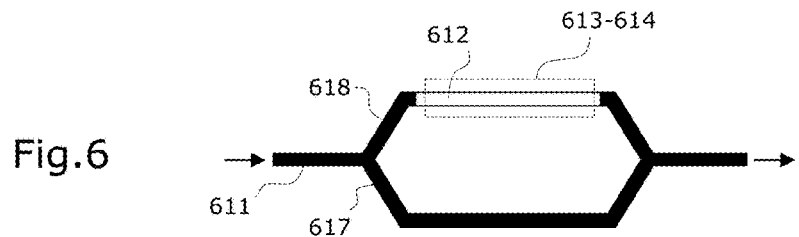

In FIG. 6, the optical circuit comprises an optical guide 611 including a Mach-Zehnder interferometer formed by two branches 617 and 618 parallel with each other, of the same refraction and the same length. One 618 of these branches includes the coupling portion 612 on which a group of nanotubes is deposited, forming a detection zone 613 or 614. A signal is for example injected on the left side and propagates in the two branches 617 and 618. Depending on the presence or absence of molecules of the target product corresponding to the receptor grafted onto the nanotubes, the photonic characteristics of the coupling portion 612 are modified, in particular the refractive index. The optical signal in this branch 618 is thus modified, in particular in its phase, and interferes with the signal originating from the other branch 617 to provide an output signal which is modified, in particular in its intensity.

Figure 8A:
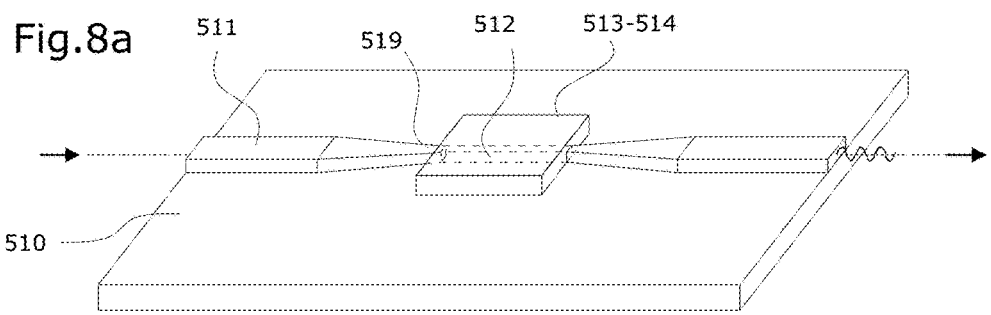
FIG. 8a and FIG. 8b are schematic diagrams illustrating an example configuration of the optical guide around the coupling portion in embodiments using a coupling on a straight optical guide part, with narrowings and with photonic crystals respectively.
Figure 8B:
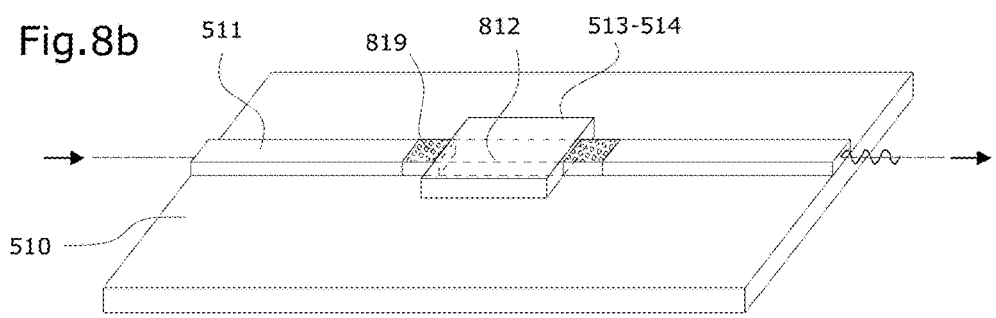

As illustrated in FIG. 8a, the coupling portion 512, 612 is preferably formed in a part of the optical guide 511, 611 which has a form determining an evanescent optical mode, here a narrow constant section part 519 situated between a narrowing and a widening of a straight guide 511, 611 of FIG. 5 or FIG. 6. FIG. 8b illustrates a variant in which the evanescent optical mode is obtained by a coupling part 812 which can be of the same width and having vertical through holes 819 arranged to form a photonic crystal in this coupling portion.

Figure 7:
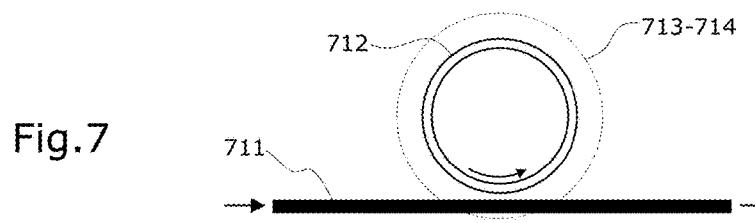
Figure 9:
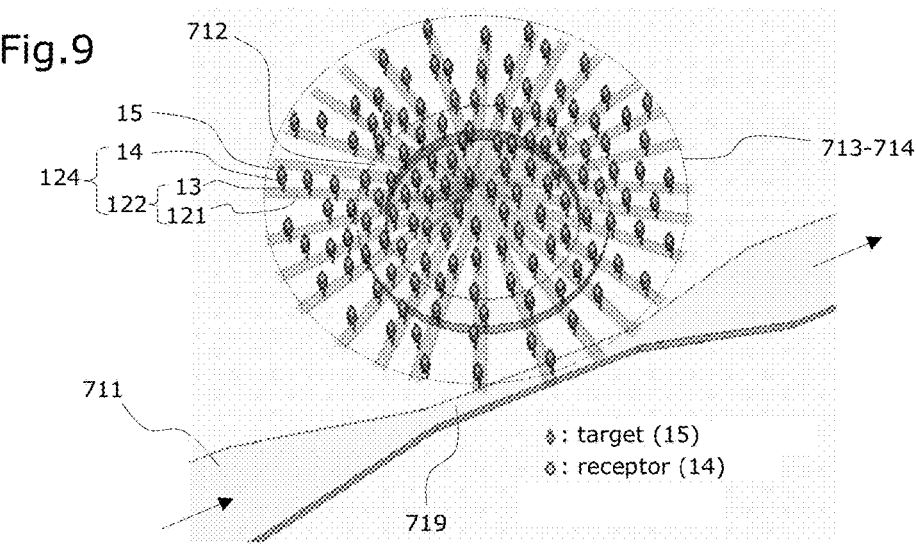
FIG. 9 is a schematic diagram illustrating an example configuration of the optical guide around the coupling portion in embodiments comprising a ring resonator.

In FIG. 7 and FIG. 9, the circuit comprises a straight optical guide 711 adjacent to a closed loop and thus forms a ring resonator. The closed loop serves as a whole or part coupling portion 712 and, for this, comprises functionalized and finalized nanotubes, for example arranged radially as illustrated in FIG. 9, thus forming an annular or disc-shaped detection zone 714.

A signal is injected into the main guide 711, for example on the left side, and transmitted by optical coupling at a narrow part 719 in the loop 712 where it resonates. This resonance depends on the photonic characteristics of this loop, for example the refractive index, resulting from the optical coupling between the guide portion 712 and the nanotubes of the detection zone 714. The characteristics of the output signal are thus modified by the presence or absence of molecules of the target product corresponding to the receptor grafted onto the nanotubes.

As illustrated in FIG. 9, the finalized nanotubes 122 are preferably, but not necessarily, arranged across the coupling portion 712, therefore radially in the case of a circular loop, for example by dielectrophoresis.

Figure 10:
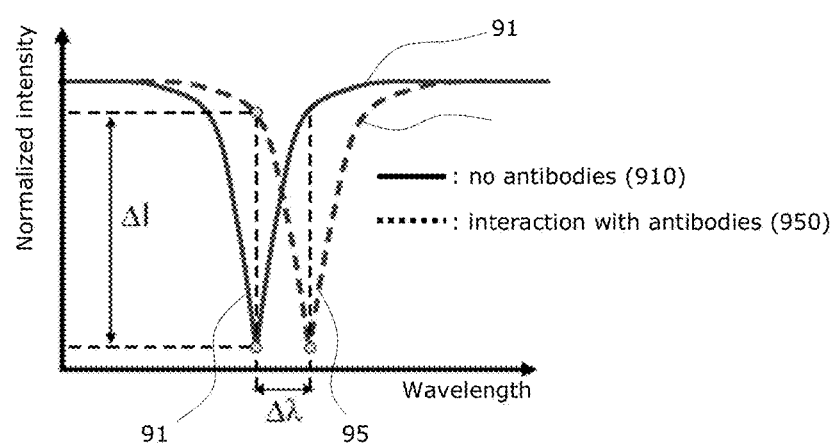
FIG. 10 is a simplified curve illustrating an example response of the sensor in FIG. 9 in an embodiment using presence detection by phase variation.

FIG. 10 thus represents a type of response which can be obtained in a sensor with a ring resonator as illustrated in FIG. 7 or FIG. 9. The continuous curve 910 obtained in the absence of the antibodies to be tested shows a peak 91 decreasing in intensity by a value $\Delta I$ at the resonator outlet. In the presence of antibodies 15 binding to the receptors 14 borne by the nanotubes 122 of the detection zone 714, the modification of the refractivity of the loop 712 coupled to the nanotubes varies the propagation phase of the signal in the loop, and produces a dotted-line curve 950 in which the peak decreasing in intensity 95 is shifted by a value $\Delta\lambda$. The detection of this shift by an operating device 190 thus makes it possible to detect antibodies 15, or even to measure the quantity thereof.

Figure 11A:
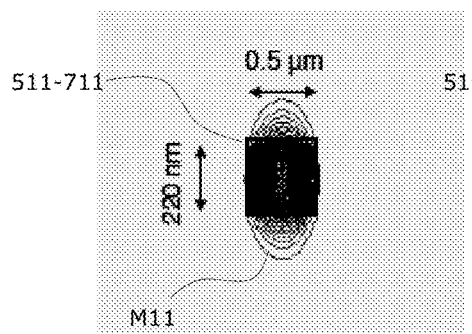
FIG. 11a and FIG. 11b are schematic diagrams illustrating the evanescent effect in a reduction in width of the optical guide, with examples of dimensions of the narrowed portion of the optical guide, in the case of a sensor according to the invention.
Figure 11B:
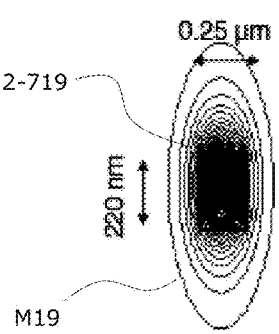

These optical circuits 111, 511, 611, 711 preferably comprise a waveguide band with a variable width so as to control the evanescent field and optimize the interaction with the surrounding carbon nanotubes. As illustrated in FIG. 11a and FIG. 11b, for the same height of waveguide, for example 220 nm, a reduction by half of the width makes it possible to obtain an optical mode the field M11 of which widens in particular M19 in the direction of the height of the waveguide, which promotes the coupling with the functionalized nanotube or nanotubes 122, 14 which surround it. This reduction can be for example by half, from 0.5 μm in the case of the waveguide 511, 711 in FIG. 11a to 0.25 μm (or even 0.15 μm or less) in the case of the narrow part 519, 719 in FIG. 11b.

The injected and/or detected wavelength is adjusted depending on the chirality chosen for the carbon nanotubes, or vice versa. The chosen wavelength can be for example 1.3 μm, a value at which the optical absorption of the gels or aqueous solutions is limited or even negligible, with which for example nanotubes of type (8, 7) will be used.

FIG. 12a to FIG. 12e illustrate different examples of positioning of the nanotubes 122 with respect to the coupling portion 112, 512, 612, 712 of the optical guide.

The nanotubes 122 can be aligned with each other, for example by dielectrophoresis, parallel in the case of the straight coupling portions 112, 512, 612 or radially in the case of a curved coupling portion 712.

Figure 12A:
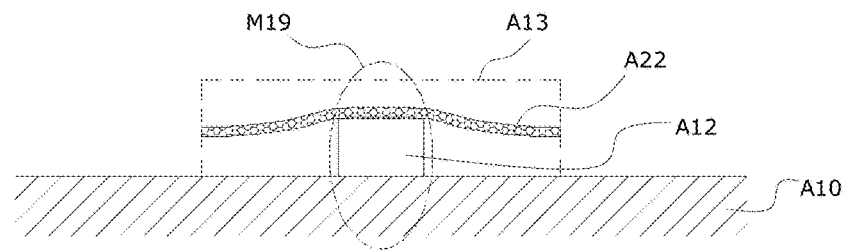
FIG. 12a to FIG. 12f are schematic diagrams of a cross-section through the coupling portion, illustrating different examples of positioning of the nanotubes with respect to the optical guide.

As illustrated in FIG. 12a, certain embodiments can comprise a group A13 constituted by a single nanotube A22 forming part of the optical mode M19 determined by the coupling portion A12, in all the configurations described hereafter.

For these different configurations, the content of the "group" of nanotube(s) is represented by neutral shading as the number of nanotubes, and their alignment or non-alignment, can vary according to the embodiments.

Figure 12B:
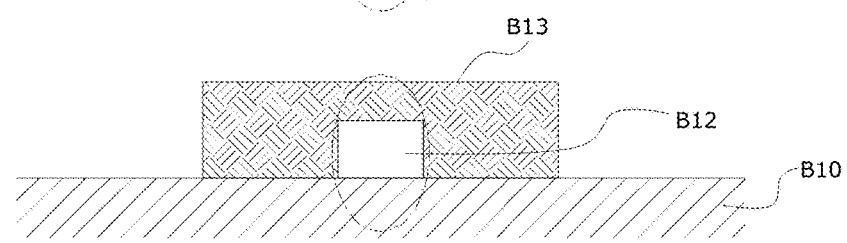

In FIG. 12b, the group B13 is deposited on top of the coupling portion B12, which rests on top of the substrate B10.

Figure 12C:
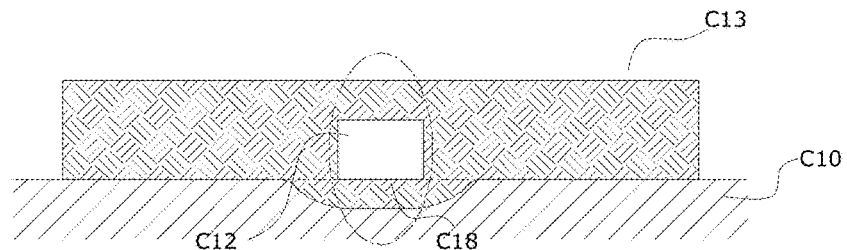

In FIG. 12c, the group C13 is deposited on the coupling portion C12, and also intrudes below by means of under-etching C18 produced in the substrate C10.

Figure 12D:
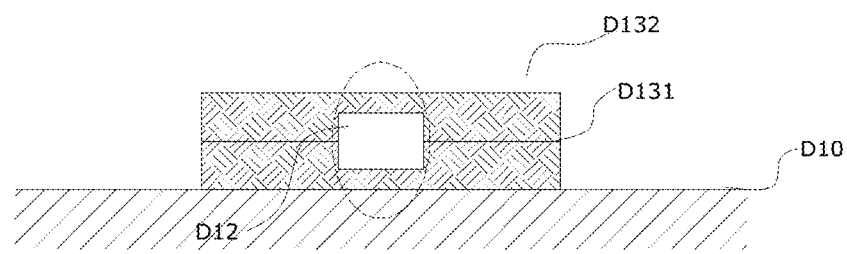

In FIG. 12d, the group comprises a first layer D131 of nanotube(s) deposited on the substrate D10 under the coupling portion D12, itself surmounted by a second layer D132 of nanotube(s).

Figure 12E:
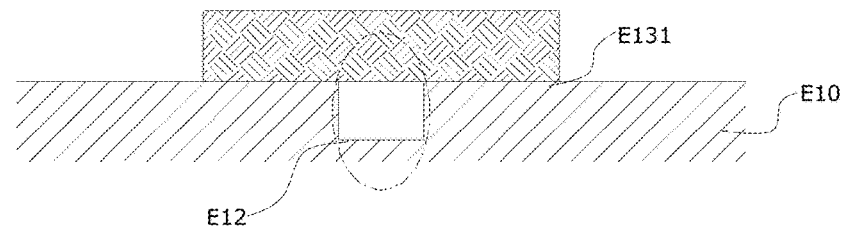

In FIG. 12e, the group E13 is deposited on the coupling portion E12, which is wholly or partly embedded in a groove within substrate E10.

Figure 12F:
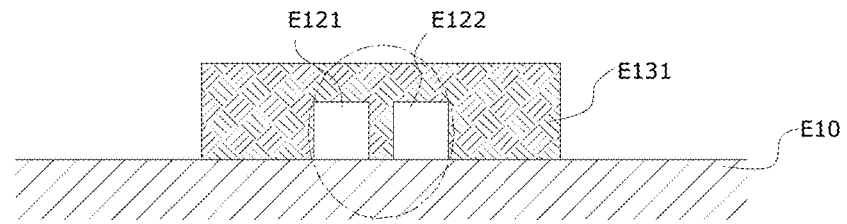

In FIG. 12f, the coupling portion comprises two parts F121 and F122 substantially parallel with each other resting on the substrate F10, on which the group F13 is deposited. This splitting of the coupling portion can also be used in all the other configurations shown in FIG. 12a to FIG. 12e.

Of course, the invention is not limited to the examples which have just been described and numerous adjustments can be made to these examples without exceeding the scope of the invention.

The invention claimed is:

1. A component for detecting or measuring at least one specific type of biological or chemical product called a target product and supplying a light signal or electronic signal representing the presence of said target product in a biological or chemical medium to be tested, when said medium to be tested is brought into contact with a sensor, the component comprising:
   at least one optical waveguide element associated with the sensor, wherein the operation of said at least one optical waveguide is modified by the presence of said target product in the medium to be tested;
   one or more nanotubes configured to interact with said target product due to molecules called receptors which are chosen to specifically interact with or bind to said target product and are bound to said one or more nanotubes via molecules or chains of molecules of at least one polymer, called a functionalization polymer, bound to the surface of said one or more nanotubes one or more optical characteristics of said one or more nanotubes being modified by said functionalization polymer;
   said one or more nanotubes surrounding said at least one optical waveguide element over at least part of its periphery and inducing an optical coupling in a coupling portion of said at least one optical waveguide, between:
      an optical signal transmitted or received in said coupling portion of said at least one optical waveguide, and
      one or more optical characteristics of said one or more nanotubes;
   wherein the coupling portion is enclosed in or connected to an optical element that carries out an optical amplification or an optical detection of said modifications of the optical characteristics of the nanotubes; and
   wherein detecting or measuring said at least one target product is provided through said detection of the modifications of the optical characteristics of the nanotubes.

2. The component according to claim 1, wherein the functionalization polymer receives a plurality receptors, associated with different target products.

3. The component according to claim 1, wherein the one or more nanotubes in the group are single-walled carbon nanotubes of semiconducting type.

4. The component according to claim 1, wherein the coupling portion of the at least one optical waveguide is arranged to obtain an evanescent mode which confines the electromagnetic wave around at least some of the nanotubes.

5. The component according to claim 1, wherein the at least one optical waveguide is made of silicon or silicon nitride.

6. The component according to claim 1, wherein the coupling portion is enclosed in or connected to an optical element that carries out an optical amplification or an optical detection of the modifications of the optical characteristics of the nanotubes originating from the interaction with the target product.

7. The component according to claim 1, wherein the at least one optical waveguide is produced on a base or a substrate by a photonic or optronic circuit manufacturing procedure.

8. A device for detecting at least one specific type of biological or chemical product called target, for example in liquid or gaseous form, comprising: a plurality of sensors each including at least one component according to claim 1 arranged so as to interact simultaneously and independently of each other with the same medium to be tested.

9. The device according to claim 8, characterized in that at least two of the sensors are functionalized in order to detect or measure two different target products.

10. The method for detecting or measuring at least one specific type of biological or chemical product called a target, comprising a use of the component according to claim 1.

11. The method for detecting or measuring a plurality of different types of biological or chemical products called a target, for example in liquid or gaseous form, comprising a use of a device according to claim 8.

* * * * *